United States Patent
Volp et al.

(10) Patent No.: US 10,968,197 B2
(45) Date of Patent: Apr. 6, 2021

(54) PHOTOINITIATORS WITH PROTECTED CARBONYL GROUP

(71) Applicant: 3M INNOVATIVE PROPERTIES COMPANY, St. Paul, MN (US)

(72) Inventors: Kelly A. Volp, Minneapolis, MN (US); Shih-Hung Chou, Maplewood, MN (US); Paul J. Homnick, Lake Elmo, MN (US); Ahmed S. Abuelyaman, Woodbury, MN (US); Tao Gong, Woodbury, MN (US); Joel D. Oxman, Minneapolis, MN (US); Wayne S. Mahoney, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 228 days.

(21) Appl. No.: 16/338,605

(22) PCT Filed: Oct. 9, 2017

(86) PCT No.: PCT/US2017/055697
§ 371 (c)(1),
(2) Date: Apr. 1, 2019

(87) PCT Pub. No.: WO2018/075275
PCT Pub. Date: Apr. 26, 2018

(65) Prior Publication Data
US 2019/0248757 A1    Aug. 15, 2019

Related U.S. Application Data

(60) Provisional application No. 62/410,419, filed on Oct. 20, 2016.

(51) Int. Cl.
| | | |
|---|---|---|
| *C07D 317/26* | (2006.01) | |
| *C07D 319/06* | (2006.01) | |
| *A61K 6/30* | (2020.01) | |
| *A61K 6/62* | (2020.01) | |
| *A61K 6/887* | (2020.01) | |
| *C08F 2/50* | (2006.01) | |
| *A61K 6/71* | (2020.01) | |
| *C08L 33/10* | (2006.01) | |

(52) U.S. Cl.
CPC .............. *C07D 317/26* (2013.01); *A61K 6/30* (2020.01); *A61K 6/62* (2020.01); *A61K 6/887* (2020.01); *C07D 319/06* (2013.01); *C08F 2/50* (2013.01); *A61K 6/71* (2020.01); *C08L 33/10* (2013.01)

(58) Field of Classification Search
None
See application file for complete search history.

(56) References Cited

U.S. PATENT DOCUMENTS

| | | |
|---|---|---|
| 2,801,185 A | 7/1957 | Iler |
| 4,503,169 A | 3/1985 | Randklev |
| 4,522,958 A | 6/1985 | Das |
| 4,619,979 A | 10/1986 | Kotnour |
| 4,843,134 A | 6/1989 | Kotnour |
| 5,130,347 A | 7/1992 | Mitra |
| 5,154,762 A | 10/1992 | Mitra |
| 5,637,646 A | 6/1997 | Ellis |
| 5,804,610 A | 9/1998 | Hamer |
| 5,925,715 A | 7/1999 | Mitra |
| 5,962,550 A | 10/1999 | Akahane |
| 6,126,922 A | 10/2000 | Rozzi |
| 6,387,981 B1 | 5/2002 | Zhang |
| 6,572,693 B1 | 6/2003 | Wu |
| 6,586,483 B2 | 7/2003 | Kolb |
| 6,670,436 B2 | 12/2003 | Burgath |
| 6,730,156 B1 | 5/2004 | Windisch |
| 6,794,520 B1 | 9/2004 | Moszner |
| 7,074,839 B2 | 7/2006 | Fansler |
| 7,090,721 B2 | 8/2006 | Craig |
| 7,090,722 B2 | 8/2006 | Budd |
| 7,134,875 B2 | 11/2006 | Oxman |
| 7,156,911 B2 | 1/2007 | Kangas |
| 7,241,437 B2 | 7/2007 | Davidson |
| 7,342,047 B2 | 3/2008 | Lewandowski |
| 7,598,298 B2 | 10/2009 | Lewandowski |
| 7,605,190 B2 | 10/2009 | Moszner |
| 7,649,029 B2 | 1/2010 | Kolb |
| 7,674,850 B2 | 3/2010 | Karim |
| 7,714,034 B2 | 5/2010 | Moszner |
| 7,888,400 B2 | 2/2011 | Abuelyaman |

(Continued)

FOREIGN PATENT DOCUMENTS

| | | |
|---|---|---|
| EP | 0334338 | 9/1989 |
| EP | 0336417 | 10/1989 |

(Continued)

OTHER PUBLICATIONS

Adamo, "Toward reliable density functional methods without adjustable parameters: The PBE0 model", J. Chem. Phys., 1999, vol. 110, No. 13, pp. 6158-6170.

(Continued)

*Primary Examiner* — Robert T Butcher

(57) ABSTRACT

Disclosed are of the protected photoinitiators of the formula: wherein Aryl1 is an aromatic or heteroaromatic ring; Aryl2 is an aromatic ring; each $R^1$ is an alkyl, an aryl, an electron donating group or an electron withdrawing group, and subscript a is 0 to 3; each $R^2$ is an alkyl, an aryl, an electron donating group or an electron withdrawing group, and subscript b is 0 to 3; Prot is a protected carbonyl group.

$$\text{Aryl}^1\underset{(R^1)_a}{\underset{|}{\phantom{X}}}\overset{\displaystyle O}{\overset{\displaystyle \|}{C}}\overset{\displaystyle O}{\overset{\displaystyle \|}{C}}\overset{\displaystyle \text{Prot}}{\overset{\displaystyle |}{C}}\underset{(R^2)_b}{\underset{|}{\phantom{X}}}\text{Aryl}^2 \quad \text{I}$$

21 Claims, 1 Drawing Sheet

(56) References Cited

U.S. PATENT DOCUMENTS

| | | | |
|---|---|---|---|
| 8,426,490 | B2 | 4/2013 | Bissinger |
| 8,710,113 | B2 | 4/2014 | Eckert |
| 8,829,067 | B2 | 9/2014 | Moszner |
| 9,012,531 | B2 | 4/2015 | Abuelyaman |
| 9,173,820 | B2 | 11/2015 | Eckert |
| 9,237,990 | B2 | 1/2016 | Abuelyaman |
| 9,333,150 | B2 | 5/2016 | Moszner |
| 2001/0030307 | A1 | 10/2001 | Bergstrom |
| 2003/0063804 | A1 | 4/2003 | Henry |
| 2005/0017966 | A1 | 1/2005 | Engl |
| 2010/0021869 | A1 | 1/2010 | Abuelyaman |
| 2011/0041736 | A1 | 2/2011 | Gartner |
| 2015/0284601 | A1 | 10/2015 | Yurt |

FOREIGN PATENT DOCUMENTS

| | | |
|---|---|---|
| EP | 1772774 | 4/2007 |
| EP | 2401998 | 1/2012 |
| EP | 2743267 | 6/2014 |
| WO | WO 2001-030305 | 5/2001 |
| WO | WO 2008-082881 | 7/2008 |
| WO | WO 2014-078115 | 5/2014 |
| WO | WO 2015-167819 | 11/2015 |
| WO | WO 2016-133669 | 8/2016 |
| WO | WO 2017-095704 | 6/2017 |

OTHER PUBLICATIONS

Becke, "Density-functional thermochemistry. III. The role of exact exchange", J. Chem. Phys., vol. 98, No. 7, pp. 5648-5652.

Bochevarov, "Jaguar: A high-performance quantum chemistry software program with strengths in life and material sciences", International Journal of Quantum Chemistry, 2013, vol. 113, pp. 2110-2142.

Cox, "Room temperature palladium catalyzed coupling of acyl chlorides with terminal alkynes", Chem. Commun, 2005, pp. 1037-1039.

Ernzerhof, "Assessment of the Perdew-Burke-Ernzerhof exchange-correlation functional", Journal of chemical Physics, 1999, vol. 110, pp. 5029-5036.

Jacquemin, "Ab initio investigation of the n f d* Transitions in Thiocarbonyl dyes", J. Phys. Chem. A, 2006, vol. 110, pp. 9145-9152.

Larsen, "Palladium-catalyzed heck alkynylation of benzyl chlorides", Synlett, 2006, vol. 18, pp. 2941-2946.

Matijevic, "Surface & Colloid Science", vol. 6, Wiley Interscience, 1973, 3pages.

Mo, "A DDQ-promoted metal-free cross-coupling of 1,3-diarylpropyes with hydroxyl via C—H bond activation to form C—O bond", Tetrahedron, 2011, vol. 67, pp. 4793-4799.

Srinivasan, "Preparation of 1,2-diketones: oxidation of alkynes by potassium permanganate in aqueous acetone", J.Org. Chem., 1979, vol. 44, No. 9, pp. 1574.

International Search report for PCT International Application No. PCT/US2017/055697 dated Jan. 30, 2018, 4 pages.

PHOTOINITIATORS WITH PROTECTED CARBONYL GROUP

CROSS REFERENCE TO RELATED APPLICATIONS

This application is a national stage filing under 35 U.S.C. 371 of PCT/US2017/055697, filed Oct. 9, 2017, which claims the benefit of U.S. Application No. 62/410,419, filed Oct. 20, 2016, the disclosure of which is incorporated by reference in its/their entirety herein.

FIELD OF THE INVENTION

The present disclosure is directed to novel protected photoinitiators, and polymerizable compositions containing the same. The compositions are useful in adhesives, coating sealants, shaped articles and dental materials

BACKGROUND

Photoinitiators absorb actinic radiations and form an initiating species in polymerization reactions. The photoinitiators are of essentially two types: α-cleavage (Norrish type I) and hydrogen abstraction (Norrish type II). α-cleavage types undergo cleavage to produce free radicals. Hydrogen abstraction types generate free radicals by proton transfer with a second molecule.

Norrish types I and II are known for UV initiated polymerizations, but there are few examples of Norrish type I photoinitiators for visible light. The depth of cure is a function of the wavelength of the light source; the longer wavelength of visible light are able to penetrate greater thicknesses of polymerizable resins than UV.

U.S. Pat. No. 7,134,875 (Oxman et al.) describes a process for hardening dental resins using a first hardenable composition containing a first photoinitiator with a $\lambda_{max}$ from 380 to 450 nm, followed by a second hardenable composition containing a photoinitiator having a λ max of 450 to 520 nm. Bisacylphosphine oxides are used as first photoinitiator component and α-diketones as second photoinitiator component.

U.S. Pat. No. 7,714,034 (Moszner et al.) describe polymerizable dental material which contains at least one radically-polymerizable monomer and certain bisacylphosphine oxide compounds, which absorb in the UV region and also show an absorption greater than 400 nm, so that their photolysis and radical formation can be induced by irradiation with halogen lamps customary in the dental field or also with LED lamps.

U.S. Pat. No. 8,829,067 (Moszner et al.) describes polymerizable compositions an acylgermanium compound with several germanium atoms as polymerization initiator. The initiators can be activated with UV/vis light, particularly preferably of a wavelength of 400 to 500 nm.

EP 0 334 338 describes α-cleavage types such as titanocenes, acylphosphonates, acylphosphine oxides or bisacrylphosphine oxides, are also used in light-curing dental materials. Titanocenes are however not particularly reactive and are preferably used in combination with amines and/or peroxides. EP 0 336 417 describes acylphosphonates such as e.g. benzoyl-di(2,6-dimethylphenyl)phosphonate are also, on account of their low depth of curing, preferably used in combination with a second initiator system, such as e.g. the camphorquinone/amine system.

SUMMARY

The present disclosure is directed to novel Norrish type I photoinitiators that can initiate polymerization at longer wavelengths than conventional Type I photoinitiators and which result in a high depth of cure of the monomers. The initiators are effective at low concentration and make possible a rapid curing of the monomers. The absorption of the photoinitiators can be matched with the wavelength (λ) of the light source to ensure that 1) the photoinitiator absorbs the light and 2) that a bond cleavage occurs as result of the light absorbed and hence generate a radical capable of initiating a polymerization.

The photoinitiators further avoid coloration of the resulting polymers, as is common with Norrish type II photoinitiators, as the cleavage products are not colored.

In particular, this disclosure provides a protected photoinitiator of the formula:

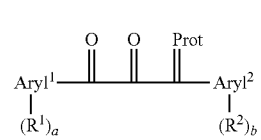

wherein
Aryl$^1$ is an aromatic or heteroaromatic ring.
Aryl$^2$ is an aromatic ring,
each R$^1$ is an alkyl, an aryl, an electron donating group or an electron withdrawing group, and subscript a is 0 to 3;
each R$^2$ is an alkyl, an aryl, an electron donating group or an electron withdrawing group, and subscript b is 0 to 3;
Prot is a protected carbonyl group.

The instant photoinitiators have a lambda max at longer wavelengths that overlaps or matches the lambda range of the light source and may be red-shifted relative to conventional Type I photoinitiators in order to accomplish that goal. In some embodiments the photoinitiators have a lambda max of about 275 nm, and an absorption including 380 to 400 nanometers. The λ max may be varied by selection of the Aryl$^1$, Aryl$^2$, R$^1$ and R$^2$ groups of Formula I.

The present disclosure further provides polymerizable compositions comprising one of more free-radically polymerizable monomers. Such compositions may be coated on a suitable substrate and photopolymerized. Such compositions may be partially polymerized to a coatable viscosity, then further photopolymerized.

DETAILED DESCRIPTION

Figure 1:
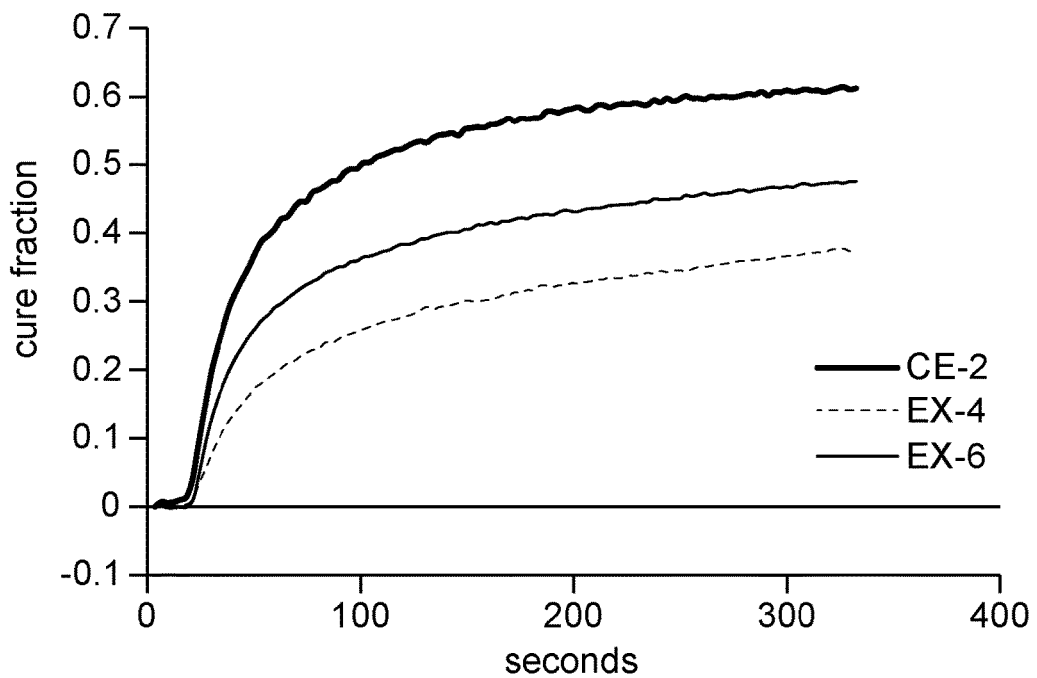
FIG. 1 is the IR spectra of a polymerization using the protected photoinitiators of Examples 4 and 6.

Novel photoinitiators of Formula I and polymerizable compositions containing the photoinitiators are provided.
In some embodiments, Aryl$^1$ is selected from

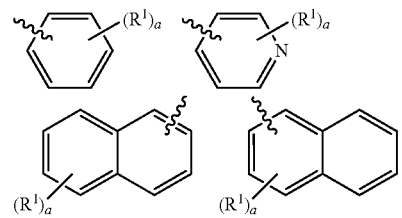

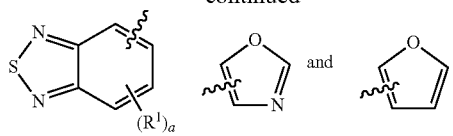

Preferably Aryl$^1$ and Aryl$^2$ are selected from phenyl and naphthyl. The "~" represent that the indicated aryl group may be attached to any carbon atom of the ring with the rest of the molecule.

Each R$^1$ and R$^2$ may be individually selected from an alkyl, an aryl, an electron donating group or an electron withdrawing group, and subscripts a and b are 0 to 3. Combinations of R$^1$ and R$^2$ groups are contemplated. For example, one or more R$^1$ groups may be alkyl and one or more an electron withdrawing groups.

In some embodiments R$^1$ and R$^2$ may be selected from electron donating group or an electron withdrawing groups. Such substituents may be used to shift the absorbance maximum (lambda max) to longer and shorter wavelengths and enable polymerization at different wavelengths. As used herein, the term "electron donating" refers to a substituent that can donate electrons. Suitable examples include, but are not limited to, a primary amino, secondary amino, tertiary amino, morpholino, hydroxy, alkoxy, aryloxy, alkyl, or combinations thereof. As used herein, the term "electron withdrawing" refers to a substituent that can withdraw electrons. Suitable examples include, but are not limited to, a halo, cyano, fluoroalkyl, perfluoroalkyl, carboxy, aminocarbonyl, alkoxycarbonyl, aryloxycarbonyl, halocarbonyl, formyl, carbonyl, sulfo, alkoxysulfonyl, aryloxysulfonyl, perfluoroalkylsulfonyl, alkyl sulfonyl, azo, alkenyl, alkynyl, dialkylphosphonato, diarylphosphonato, or combinations thereof.

In some preferred embodiments, the photoinitiators of Formula I are selected such that at least one R$^1$ is an electron withdrawing group. In some embodiments, at least one R$^2$ is selected from electron donating groups. Compounds of Formula I in which at least one R$^1$ is an electron withdrawing group and at least one R$^2$ is selected from electron donating groups. Such groups are preferentially at the ortho- or para-positions of the aromatic rings.

The carbonyl protecting group (Prot) of Formula I may be any known in the art, and which are preferably photolabile. Reference may be made to P. G. M. Wuts, *Greene's Protective Groups in Organic Synthesis*, 5th Edition, Wiley Interscience, NY, pp 554-684. Useful carbonyl protecting groups may be selected from ketals (including cyclic ketals), monothioketals, dithioketals, O-substituted cyanohydrins, substituted hydrazones, oxazolidines, imidazolidines acylals, imines (derived from primary amines such as aniline and benzylamine), oximes and thiazolidines. Preferred are those protecting groups that may be cleaved photolytically, such as ketals. Other protecting groups not photolytically cleaved by be deprotected as is known in the art.

In general, compounds of Formula I may be prepared by coupling of an aromatic acetylide compound with an aromatic methylene halide compound, followed by oxidative ketalization, and oxidation of the alkyne to a diketone:

Scheme 1

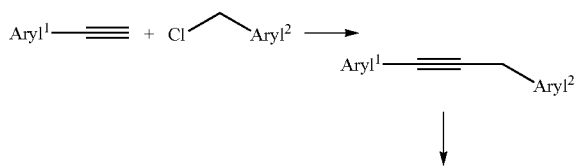

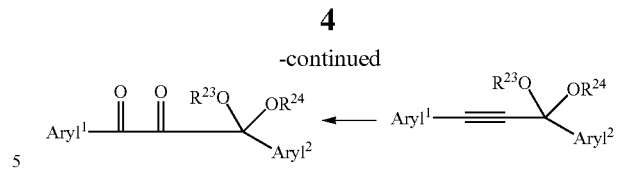

wherein R$^{23}$ and R$^{24}$ are C$_1$-C$_4$ alkyl, or may be taken together to form a five- or six-member cyclic ketal, and Aryl$^1$ and Aryl$^2$ are as previously defined. It will be appreciated that other carbonyl protecting groups may be used in the above Scheme.

The Heck coupling in the first step is described in C. H. Larsen et al., SynLett 2006, vol. 18, 2941-2946. The second step of oxidative ketalization is described in H. Mo et al., Tetrahedron 2011, vol. 67, 4793-4799. The third step of oxidation of the alkyne to a diketone is described in N. S. Srinivasan et al., J. Org. Chem., 1979, vol. 44, 1574.

Alternatively, the compounds of Formula I may be prepared by coupling of an aryl alkyne with an aryl acyl halide, followed by ketalization, then oxidation of the alkyne to a diketone.

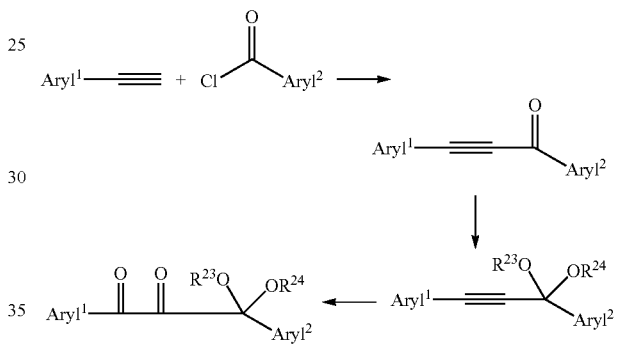

The present disclosure further provides a polymerizable composition comprising the photoinitiator and at least one polymerizable component monomer, such as vinyl monomers, and (meth)acryloyl monomers (including acrylate esters, amides, and acids to produce (meth)acrylate homo- and copolymers). The photoinitiator is present in the composition in amounts, from about 0.1 to about 10 parts by weight, preferably 0.1 to 5 parts by weight, based on 100 parts by weight of the polymerizable component of the polymerizable composition.

In some embodiments, the polymerizable composition comprises the photoinitiator and one or more vinyl monomers. Vinyl monomers useful in the polymerizable composition include vinyl ethers (e.g. methyl vinyl ether, ethyl vinyl ether), vinyl esters (e.g., vinyl acetate and vinyl propionate), styrene, substituted styrene (e.g., α-methyl styrene), vinyl halide, divinylbenzene, alkenes (e.g. propylene, isomers of butylene, pentene, hexylene up to dodecene, isoprene, butadiene) and mixtures thereof.

In some embodiments the polymerizable composition comprises one or more (meth)acrylate ester monomer(s). (Meth)acrylate ester monomer useful in preparing (meth)acrylate (co)polymers are monomeric (meth)acrylic ester of a non-tertiary alcohol, which alcohol contains from 1 to 14 carbon atoms and preferably an average of from 4 to 12 carbon atoms.

Examples of monomers suitable for use as the (meth) acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomers are suitable. In some embodiments, the preferred (meth)acrylate ester monomer is the ester of (meth)acrylic acid with an alcohol derived from a renewable source, such as 2-octanol, citronellol, or dihydrocitronellol.

The polymerizable composition may comprise an acid functional monomer, where the acid functional group may be an acid per se, such as a carboxylic acid, or a portion may be a salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic or phosphoric acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

The polymerizable composition may comprise a polar monomer. The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; tetrahydrofurfuryl (meth)acrylate, poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of tetrahydrofurfuryl (meth)acrylate, 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

The polymerizable composition may further comprise a vinyl monomer when preparing acrylic copolymers. When used, vinyl monomers useful in the (meth)acrylate polymer include vinyl esters (e.g., vinyl acetate and vinyl propionate), styrene, substituted styrene (e.g., α-methyl styrene), vinyl halide, divinylbenzene, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer when preparing acrylic copolymers.

A multifunctional (meth)acrylate may be incorporated into the blend of polymerizable monomers. Examples of useful multifunctional (meth)acrylates include, but are not limited to, di(meth)acrylates, tri(meth)acrylates, and tetra (meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth) acrylate is tailored depending upon application of the adhesive composition, for example, adhesives, hardcoats or dental resins.

Typically, the multifunctional (meth)acrylate is present in amounts up to 100 parts, preferably 0.1 to 100 parts, based 100 parts by weight of remaining polymerizable monofunctional monomers. In some embodiments the multifunctional (meth)acrylate is used in amounts of greater than 50 parts by weight, based on the 100 parts by weight of remaining polymerizable monomers. In some embodiments, the multifunctional (meth)acrylate may be present in amounts from 0.01 to 5 parts, preferably 0.05 to 1 parts, based on 100 parts total monomers of the polymerizable composition for adhesive applications, and greater amounts for hardcoats.

In such embodiments, an acrylic copolymer may be prepared from a polymerizable composition comprising:
i. up to 100 parts by weight, preferably 85 to 99.5 parts by weight of an (meth)acrylic acid ester;
ii. 0 to 15 parts by weight, preferably 0.5 to 15 parts by weight of an acid functional ethylenically unsaturated monomer;
iii. 0 to 15 parts by weight of a non-acid functional, ethylenically unsaturated polar monomer;
iv. 0 to 5 parts by weight vinyl monomer;
v. 0 to 100 parts by weight of a multifunctional (meth) acrylate, preferably 50 to 100 parts by weight, relative to i-iv;
and
vi. the photoinitiator in amounts from about 0.1 weight percent to about 5.0 weight percent, relative to 100 parts total monomer i-v.

The present polymerizable compositions are also useful in the preparation of hardcoats and structural or semi-structural adhesives. The term "hardcoat" or "hardcoat layer" means a layer or coating that is located on the external surface of an object, where the layer or coating has been designed to at least protect the object from abrasion.

The present disclosure provides hardcoat compositions comprising the photoinitiator system and a multifunctional (meth)acrylate monomer comprising two (preferably three) or more (meth)acrylate groups, and/or a multifunctional (meth)acrylate oligomer and optionally a (meth)acrylate-functional diluent.

Useful multifunctional (meth)acrylate monomers comprise three or more (meth)acrylate groups. Multifunctional (meth)acrylate monomers are useful in the practice of the present invention because they add abrasion resistance to the hard coat layer. Preferred multifunctional (meth)acrylate monomers comprising three or more (meth)acrylate groups include trimethylol propane tri(meth)acrylate (TMPTA), pentaerythritol tri(meth)acrylate, pentaerythritol tetra(meth) acrylate, dipentaerithritol tri(meth)acrylate (Sartomer 355), dipentaerythritol penta(meth)acrylate (Sartomer 399), dipentaerythritol hydroxy penta(meth)acrylate (DPHPA), glyceryl propoxy tri(meth)acrylate, trimethylolpropane tri (meth)acrylate, and mixtures thereof. Another useful radiation-curable component of the present invention is the class of multifunctional (meth)acrylate oligomers, having two or more (meth)acrylate groups, and having an average molecular weight (Mw) in the range from about 400 to 2000.

Useful multifunctional (meth)acrylate oligomers include polyester (meth)acrylates, polyurethane (meth)acrylates, and (meth)acrylated epoxy (meth)acrylates. (Meth)acrylated epoxy (meth)acrylates and polyester(meth)acrylates are most preferred because they tend to have a relatively low viscosity and therefore allow a more uniform layer to be applied by the spin coating method. Specifically, preferred multifunctional (meth)acrylate oligomers include those commercially available from UCB Radcure, Inc. of Smyrna, Ga. and sold under the trade name Ebecryl (Eb): Eb40 (tetrafunctional acrylated polyester oligomer), ENO (polyester tetra-functional (meth)acrylate oligomer), Eb81 (multifunctional (meth)acrylated polyester oligomer), Eb600 (bisphenol A epoxy di(meth)acrylate), Eb605 (bisphenol A epoxy di(meth)acrylate diluted with 25% tripropylene glycol di(meth)acrylate), Eb639 (novolac polyester oligomer), Eb2047 (trifunctional acrylated polyester oligomer), Eb3500 (di-functional Bisphenol-A oligomer acrylate), Eb3604 (multi-functional polyester oligomer acrylate), Eb6602 (trifunctional aromatic urethane acrylate oligomer), Eb8301 (hexafunctional aliphatic urethane acrylate), EbW2 (difunctional aliphatic urethane acrylate oligomer), and mixtures thereof. Of these, the most preferred are, Eb 600, Eb605, Eb80, and Eb81.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art.

In some embodiments, the multifunctional (meth)acrylate oligomers may comprise a reactive oligomer having pendent polymerizable groups comprising:
a) greater than 50 parts by weight, preferably greater than 75 parts by weight, most preferably greater than 80 parts by weight of (meth)acrylate ester monomer units;
b) 1 to 10 parts by weight, preferably 1 to 5 parts by weight, most preferably 1 to 3 parts by weight, of monomer units having a pendent, free-radically polymerizable functional group,
c) 0 to 20 parts by weight of other polar monomer units, wherein the sum of the monomer units is 100 parts by weight.

The reactive oligomer may be represented by the formula:

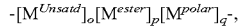

$-[M^{Unsatd}]_o[M^{ester}]_p[M^{polar}]_q-$,    II where
$[M^{Unsatd}]$ represents monomer units having a pendent, free-radically polymerizable functional groups and subscript "o" is the parts be weight thereof;
$[M^{ester}]$ represents (meth)acrylate ester monomer units and subscript "p" represents the parts by weight thereof; and
$[M^{polar}]$ represents polar monomer units and subscript "q" represents the parts by weight thereof.

The reactive oligomers (II) of the composition comprise one or more pendent groups that include free-radically polymerizable unsaturation, including (meth)acryloyl, (meth)acryloxy, propargyl, vinyl, allyl, acetylenyl and (meth)acrylamide. That is, the monomer units $[M^{Unsatd}]$ contain such polymerizable groups.

The reactive oligomer may be photopolymerized per se, or with a multifunctional acrylate, such as hexanediol di(meth)acrylate. The reactive oligomer having pendent polymerizable groups may be prepared as described in U.S. Pat. No. 7,598,298 (Lewandowski et al.), U.S. Pat. No. 7,342,047 (Lewandowski et al.) and U.S. Pat. No. 7,074,839 (Fansler et al.), each incorporated herein by reference.

The polymerizable reactive oligomer component may further comprise a diluent monomer. The (meth)acrylate-functional diluents, also referred to herein as "reactive diluents", are relatively low molecular weight mono- or di-functional, non-aromatic, (meth)acrylate monomers. These relatively low molecular weight reactive diluents are advantageously of a relatively low viscosity, e.g., less than about 30 centipoise (cps) at 25° C. Di-functional, non-aromatic (meth)acrylates are generally preferred over mono-functional non-aromatic (meth)acrylates because di-functional non-aromatic (meth)acrylates allow for quicker cure time. Preferred reactive diluents include 1,6-hexanediol di(meth)acrylate (HDDA from UCB Radcure, Inc. of Smyrna, Ga.), tripropylene glycol di(meth)acrylate, isobornyl (meth)acrylate (1130A, Radcure), 2(2-ethoxyethoxy) ethyl (meth)acrylate (sold under the trade name Sartomer 256 from SARTOMER Company, Inc. of Exton, Pa.), n-vinyl formamide (Sartomer 497), tetrahydrofurfuryl (meth) acrylate (Sartomer 285), polyethylene glycol di(meth)acrylate (Sartomer 344), tripropylene glycol di(meth)acrylate (Radcure), neopentyl glycol dialkoxy di(meth)acrylate, polyethyleneglycol di(meth)acrylate, and mixtures thereof.

In some embodiments the polymerizable composition may comprise:
20-80 parts by weight of multifunctional (meth)acrylate monomers and/or multifunctional (meth)acrylate reactive oligomers,
0 to parts by weight range of (meth)acrylate diluent,
20 to 75 wt. % of silica (per se, whether or not functionalized), and
from about 0.1 weight percent to about 5.0 weight percent of the photoinitiator, based on the 100 parts by weight of the polymerizable components of the polymerizable composition.

In some embodiments, the polymerizable composition provides a structural and semi-structural adhesive composition in which the partially cured composition may be disposed between two substrates (or adherends), and subsequently fully cured to effect a structural or semi-structural bond between the substrates. "Semi-structural adhesives" are those cured adhesives that have an overlap shear strength of at least about 0.5 MPa, more preferably at least about 1.0 MPa, and most preferably at least about 1.5 MPa. Those cured adhesives having particularly high overlap shear strength, however, are referred to as structural adhesives. "Structural adhesives" are those cured adhesives that have an overlap shear strength of at least about 3.5 MPa, more preferably at least about 5 MPa, and most preferably at least about 7 MPa.

In some embodiments the present disclosure provides an adhesive composition comprising the photoinitiator system and a) a first reactive oligomer comprising (meth)acrylate ester monomer units, hydroxyl-functional monomer units, and monomer units having polymerizable groups; b) a second component comprising $C_2$-$C_4$ alkylene oxide repeat units and polymerizable terminal groups, and c) a diluent monomer component.

The first component reactive oligomer is of the general formula:

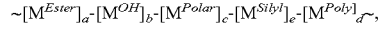

$\sim[M^{Ester}]_a-[M^{OH}]_b-[M^{Polar}]_c-[M^{Silyl}]_e-[M^{Poly}]_d\sim$, where
$[M^{Ester}]$ represents interpolymerized (meth)acrylate ester monomer units and subscript a is greater than 50 parts by weight;
$[M^{OH}]$ represents interpolymerized (meth)acryloyl monomer units having a pendent hydroxy groups where subscript b represents 0 to 20 parts by weight,
$[M^{Polar}]$ represent optional polar monomer units, where subscript c is 0-20, preferably 1-10 parts by weight,
$[M^{Silyl}]$ represent silyl functional monomer units, where subscript e is 0 to 10, preferably 1-5 parts by weight; and
$[M^{Poly}]$ represents monomer units comprising polymerizable groups silane-functional monomer units and subscript d represents 1-10 parts by weight. The sum of subscripts a to e being 100 parts by weight. Such reactive oligomers are further described in Applicant's copending US 2015/0284601 (Yurt et al., incorporated herein by reference) and in WO 2014/078115 (Behling et al.). As taught in Yurt '601, the oligomer is functionalized with the polymerizable groups ($M^{Poly}$ units) by functionalization of the pendent hydroxy groups of the $M^{OH}$ monomer. The a second component of the Yurt '601 composition is at comprising $C_2$-$C_4$ alkylene oxide units and 1 to 3 terminal polymerizable groups, such as (meth)acrylate groups.

In some embodiments the crosslinkable composition may include filler. In some embodiments the total amount of filler is at most 50 wt. %, preferably at most 30 wt. %, and more preferably at most 10 wt. % filler. Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911(Kangas et al.), and U.S. Pat. No. 7,649,029 (Kolb et al.).

In some embodiments the filler may be surface modified. A variety of conventional methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference. Filler components also include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

The polymerizable composition and the photoinitiator may be combined and irradiated with activating UV/Vis radiation to initiate the polymerization. The photopolymerization may be effected by any suitable light source including carbon arc lights, low, medium, or high pressure mercury vapor lamps, swirl-flow plasma arc lamps, xenon flash lamps, ultraviolet light emitting diodes, and ultraviolet light emitting lasers. For many applications it may be desirable to use an LED light source or array to effect the curing. Such LED sources may effect a faster cure and provide less heat to the composition during cure. One suitable LED source is the Norlux large area array, series 808 (available from Norlux, Carol Stream, Ill.). Alternatively the Omnicure™ LED light series from Excelitas Technologes, Waltham, Mass. may be used.

UV light sources can be of two types: 1) relatively low light intensity sources such as backlights which provide generally 10 mW/cm² or less (as measured in accordance with procedures approved by the United States National Institute of Standards and Technology as, for example, with a Uvimap™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm², preferably between 15 and 450 mW/cm². Where actinic radiation is used to fully or partially polymerize the polymerizable composition, high intensities and short exposure times are preferred. For example, an intensity of 600 mW/cm² and an exposure time of about 1 second may be used successfully. Intensities can range from about 0.1 to about 150 mW/cm², preferably from about 0.5 to about 100 mW/cm², and more preferably from about 0.5 to about 50 mW/cm². UV LEDs may also be used, such as a Clearstone UV LED lamp (Clearstone Technologies Inc., Hopkins, Minn. 385 nm).

The present polymerization may be conducted in bulk, or in a solvent. Solvents, preferably organic, can be used to assist in the dissolution of the initiator and initiator system in the polymerizable monomers, and as a processing aid. Preferably, such solvents are not reactive with components. It may be advantageous to prepare a concentrated solution of the transition metal complex in a small amount of solvent to simplify the preparation of the polymerizable composition.

In some embodiments, the polymerizable composition may be polymerized by syrup polymerization methods. A syrup polymer method comprises partially polymerizing monomers to produce a solute syrup polymer comprising copolymer and unpolymerized solvent monomers. The syrup polymer composition is polymerized to a useful coating viscosity, which may combined with the other components of the composition, optionally coated onto a substrate (such as a tape backing) and further polymerized. It will be understood that if a syrup polymerization method is used, additional photoinitiator is necessary to fully polymerize the solvent monomers after compounding.

Solventless polymerization methods, such as the continuous free radical polymerization method described in U.S. Pat. Nos. 4,619,979 and 4,843,134 (Kotnour et al.); the essentially adiabatic polymerization methods using a batch reactor described in U.S. Pat. No. 5,637,646 (Ellis); and, the methods described for polymerizing packaged pre-adhesive compositions described in U.S. Pat. No. 5,804,610 (Hamer et al.) may also be utilized to prepare the polymers. Preferably, the first copolymer is prepared by the adiabatic batch polymerization process wherein the total of the absolute value of any energy exchanged to or from the batch during the course of reaction will be less than about 15% of the total energy liberated due to reaction for the corresponding amount of polymerization that has occurred during the time that polymerization has occurred, as described in U.S. Pat. No. 5,637,646 (Ellis), incorporated herein by reference.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art.

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating, knife coating, and die coating. These various methods of coating allow the compositions to be placed on the substrate at variable thicknesses thus allowing a wider range of use of the compositions.

The polymerizable compositions may be coated upon a variety of flexible and inflexible substrates using conventional coating techniques to produce coated articles. Flexible substrates are defined herein as any material which is conventionally utilized as a tape backing or may be of any other flexible material. Examples include, but are not limited to, plastic films such as polypropylene, polyethylene, polyvinyl chloride, polyester (polyethylene terephthalate), polycarbonate, polymethyl(meth)acrylate (PMMA), cellulose acetate, cellulose triacetate, and ethyl cellulose. Foam backings may be used.

In some preferred embodiments, the substrate may be chosen so as to be transparent to the UV/Vis radiation used to initiate the polymerization. The coated article may then be initiated through the thickness of the transparent substrate.

In some embodiments, the substrate is a release liner to form an adhesive article of the construction substrate/adhesive layer/release liner or release liner/adhesive/release liner. The adhesive layer may be cured, uncured or partially cured. Release liners typically have low affinity for the curable composition. Exemplary release liners can be prepared from paper (e.g., Kraft paper) or other types of polymeric material. Some release liners are coated with an outer layer of a release agent such as a silicone-containing material or a fluorocarbon-containing material. Release coating can be applied by solvent or solvent-free methods The present disclosure further provides curable dental compositions comprising the photoinitiator. Although various curable dental compositions have been described, industry would find advantage in compositions having improved properties such as improved working time, and reduced stress deflection and/or reduced shrinkage while maintaining sufficient mechanical properties and depth of cure.

As used herein, "dental composition" refers to a material, optionally comprising filler, capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

The curable dental compositions comprise at least one ethylenically unsaturated resin monomer or oligomer in combination with the photoinitiator. In some embodiments, such as primers, the ethylenically unsaturated monomer may be monofunctional, having a single (e.g. terminal) ethylenically unsaturated group. In other embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

The amount of curable resin in the dental composition is a function of the desired end use (adhesives, cements, restoratives, etc.) and can be expressed with respect to the (i.e. unfilled) polymerizable resin portion of the dental composition. For favored embodiments, wherein the composition further comprises filler, the concentration of monomer can also be expressed with respect to the total (i.e. filled) composition. When the composition is free of filler, the polymerizable resin portion is the same as the total composition.

In favored embodiments, such ethylenically unsaturated groups of the curable dental resin includes (meth)acryloyl such as (meth)acrylamide and (meth)acrylate. Other ethylenically unsaturated polymerizable groups include vinyl and vinyl ethers. The ethylenically unsaturated terminal polymerizable group(s) is preferably a (meth)acrylate group, particularly for compositions that are hardened by exposure to actinic (e.g. UV and visible) radiation in the presence of the photoinitiator system. Further, methacrylate functionality is typically preferred over the acrylate functionality in curable dental compositions. The ethylenically unsaturated monomer may comprise various ethylenically unsaturated monomers, as known in the art, for use in dental compositions.

In favored embodiments, the dental composition comprises one or more dental resins having a low volume shrinkage monomer. Preferred (e.g. filled) curable dental compositions (useful for restorations such as fillings and crowns) comprise one or more low volume shrinkage resins such that the composition exhibits a Watts Shrinkage of less than about 2%, preferably no greater than 1.80%, more preferably no greater than 1.60%. In favored embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

Preferred low volume shrinkage monomers include isocyanurate resins, such as described in U.S. Pat. No. 9,237,990 (Abuelyaman et al.); tricyclodecane resins, such as described in U.S. Pat. Nos. 9,173,820, 9,012,531 and 8,426,490 (Eckert et al.); polymerizable resins having at least one cyclic allylic sulfide moiety such as described in U.S. Pat. No. 7,888,400 (Abuelyaman et al.); methylene dithiepane silane resins as described in U.S. Pat. No. 6,794,520 (Moszner et al.); and di-, tri, and/or tetra-(meth)acryloyl-containing resins such as described in U.S. 2010/021869 (Abuelyaman et al.); monomers having a $C_6$-$C_{20}$ backbones unit (U) and spacer units (S) connecting to the backbone unit via an ether linkage as described in U.S. Pat. No. 8,710,113 (Eckert et al.); each of which are incorporated herein by reference.

In favored embodiments, the majority of the unfilled polymerizable resin composition comprises one or more low volume shrinkage monomers ("Low shrinkage monomers"). For example, at least 50%, 60%, 70%, 80%, 90% or more of the unfilled polymerizable resin may comprise low volume shrinkage monomer(s).

In one embodiment, the dental composition comprises at least one isocyanurate resin. The isocyanurate resin comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated free radically polymerizable groups are generally bonded to the core or backbone unit via a (e.g. divalent) linking group.

The trivalent isocyanurate core structure generally has the formula:

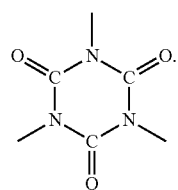

The divalent linking group comprises at least one nitrogen, oxygen or sulfur atom. Such nitrogen, oxygen or sulfur atom forms a urethane, ester, thioester, ether, or thioether linkage. Ether and especially ester linkages can be beneficial over isocyanurate resin comprising urethane linkages for providing improved properties such as reduced shrinkage, and/or increased mechanical properties, e.g., diametral tensile strength (DTS). Thus, in some embodiments, the divalent linking groups of the isocyanurate resin are free of urethane linkages. In some favored embodiments, the divalent linking group comprises an ester linkage such as an aliphatic or aromatic diester linkage.

The isocyanurate monomer typically has the general structure:

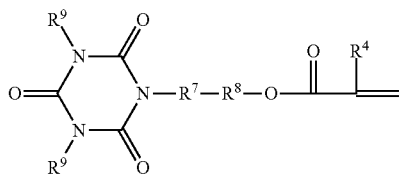

wherein $R^7$ is a (hetero)hydrocarbyl group including straight chain, branched or cyclic alkylene, arylene, or alkarylene, and optionally including a heteroatom (e.g. oxygen, nitrogen, or sulfur); $R^4$ is hydrogen or C1-C4 alkyl; $R^8$ is heterohydrocarbyl group including alkylene, arylene, or alkarylene linking group comprising at least one moiety selected from urethane, ester, thioester, ether, or thioether, and combinations of such moieties; and at least one of the $R^9$ groups is

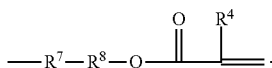

$R^7$ is typically a straight chain, branched or cyclic alkylene, optionally including a heteroatom, having no greater than 12 carbons atoms. In some favored embodiments, $R^7$ has no greater than 8, 6, or 4 carbon atoms. In some favored embodiments, $R_7$ comprises at least one hydroxyl moiety.

In some embodiments, $R^8$ comprises an aliphatic or aromatic ester linkage such as a diester linkage.

In some embodiments, $R^8$ further comprises one or more ether moieties. Hence, the linking group may comprise a combination of ester or diester moieties and one or more ether moieties.

For embodiments, wherein the isocyanurate monomer is a di(meth)acrylate monomer, $R^9$ is hydrogen, alkyl, aryl, or alkaryl, optionally including a heteroatom.

The polymerizable resin portion of the curable unfilled dental composition described herein may comprise at least 10 wt. %, 15 wt. %, 20 wt. %, or 25 wt. %, multifunctional ethylenically unsaturated isocyanurate resin(s). The isocyanurate resin may comprise a single monomer or a blend of two or more isocyanurate resins. The total amount of isocyanurate resin(s) in the unfilled polymerizable resin portion of the curable dental composition is typically no greater than 90 wt. %, 85 wt. %, 80 wt. %, or 75 wt. %.

The filled curable dental composition described herein typically comprises at least 5 wt. %, 6 wt. %, 7 wt. %, 8 wt. %, or 9 wt. % of multifunctional ethylenically unsaturated isocyanurate resin(s). The total amount of isocyanurate resin(s) of the filled hardenable (i.e. polymerizable) dental composition is typically no greater than 20 wt. %, or 19 wt. %, or 18 wt. %, or 17 wt. %, or 16 wt. %, or 15 wt. %.

In another embodiment, the dental composition comprises at least one tricyclodecane resin. The tricyclodecane resin may comprise a single monomer or a blend of two or more tricyclodecane resins. The concentration of multifunctional ethylenically unsaturated tricyclodecane monomer in the (i.e. unfilled) polymerizable resin portion or filled hardenable (i.e. polymerizable) composition can be the same as just described for the multifunctional ethylenically unsaturated isocyanurate monomer.

Tricyclodecane monomers generally have the core structure (i.e. backbone unit (U):

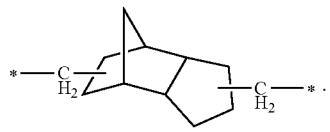

The backbone unit (U) if the tricyclodecane resin typically comprises one or two spacer unit(s) (S) bonded to the backbone unit (U) via an ether linkage. At least one spacer unit (S) comprises a $CH(R^{10})$-OG chain, wherein each group G comprises a (meth)acrylate moiety and $R^{10}$ comprises at least one group selected from hydrogen, alkyl, aryl, alkaryl and combinations thereof. In some embodiments, $R^{10}$ is hydrogen, methyl, phenyl, phenoxymethyl, and combinations thereof. G may be bonded to the spacer unit(s) (S) via a urethane moiety.

In some embodiments, the spacer unit(s) (S) typically comprise

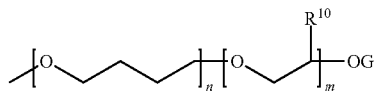

wherein m is 1 to 3; n is 1 to 3; and $R^{10}$ is hydrogen, methyl, phenyl, phenoxymethyl.

In other embodiments, the spacer unit(s) (S) typically comprise

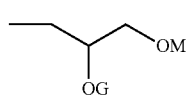

wherein M=aryl.

In some embodiments the composition comprises a multifunctional ethylenically unsaturated isocyanurate monomer and multifunctional ethylenically unsaturated tricyclodecane monomer at a weight ratio ranging from about 1.5:1 to 1:1.5.

In some embodiments, the curable dental composition comprises a polymerizable resin having at least one cyclic allylic sulfide moiety with at least one (meth)acryloyl moiety.

The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy (i.e. a (meth)acrylate moiety) or a (meth)acryloylamino (i.e., a (meth)acrylamide moiety).

In one embodiment, the low shrinkage resin includes those represented by the formulae:

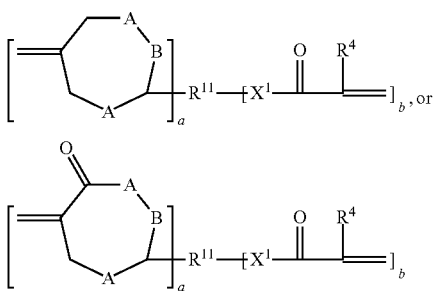

In the above formulae, each A can be independently selected from S, O, N, C (e.g., $C(R^{10})_2$, where each $R^{10}$ is independently a H or an organic group), SO, $SO_2$, N-alkyl,

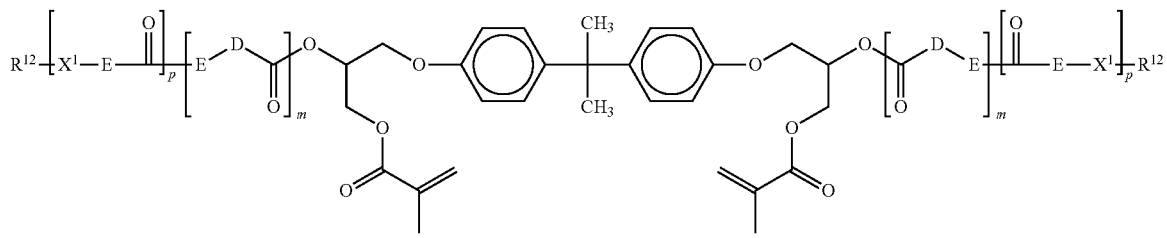

N-acyl, NH, N-aryl, carboxyl or carbonyl group, provided that at least one X is S or a group comprising S. Preferably, each A is sulfur.

B is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with B thus being either absent or methylene, respectively. In some embodiments, B is either absent or is a C1 to C3 alkylene, optionally including a heteroatom, carbonyl, acyl, or combinations thereof.

$X^1$ is independently —O— or —$NR^4$—, where $R^4$ is H or $C_1$-$C_4$ alkyl.

The $R^{11}$ group represents a linker selected from alkylene (typically having more than one carbon atom, i.e. excluding methylene), alkylene optionally including a heteroatom (e.g., O, N, S, S—S, SO, $SO_2$), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, akylthio, carbonyl, acyl, acyloxy, amido, urethane group, urea group, a cyclic allylic sulfide moiety, or combinations thereof.

$R^4$ is H or $C_1$-$C_4$ alkyl, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, akylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

The inclusion of a polymerizable compound having at least one cyclic allylic sulfide moiety can result in a synergistic combination of low volume shrinkage in combination with high diametral tensile strength.

In another embodiment, the dental composition comprises a low shrinkage resin that includes at least one di-, tri-, and/or tetra (meth)acryloyl-containing resins having the general formula:

wherein: each $X^1$ is independently —O— or —$NR^4$—, where $R^4$ is H or $C_1$-$C_4$ alkyl; D and E each independently represent an organic group, and $R^{12}$ represents —C(O)C(CH_3)=CH_2, and/or p=0 and $10^2$ represents H, —C(O)CH=CH_2, or —C(O)C(CH_3)=CH_2, with the proviso that at least one $R^{12}$ is a (meth)acrylate; each m is 1 to 5; p and q are independently 0 or 1. Although this material is a derivative of bisphenol A, when other low volume shrinkage monomer are employed, such as the isocyanurate and/or tricyclodecane monomer, the dental composition is free of (meth)acrylate monomers derived from bisphenol A. Such resins are described in WO 2008/082881 (Abuelyaman et al.)

In another embodiment, the low shrinkage dental resin may be selected from methylene dithiepane silane resins described in U.S. Pat. No. 6,794,520 (Moszner et al.), incorporated herein by reference. Such resins have the general formula

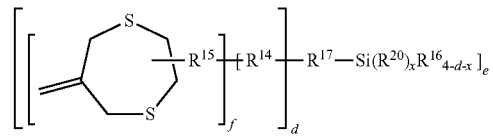

in which $R^{14}$ is a saturated or unsaturated aliphatic or alicyclic hydrocarbon radical with 1 to 10 carbon atoms, which can be interrupted by one or more oxygen and/or sulfur atoms and can contain one or more ester, carbonyl, amide and/or urethane groups, or is an aromatic or heteroaromatic hydrocarbon radical with 6 to 18 carbon atoms, the hydrocarbon radicals being able to be substituted or unsubstituted; $R^{15}$ has one of the meanings given for $R^{14}$ or is absent; $R^{16}$ has one of the meanings given for $R^{14}$ or is absent; $R^{17}$ is equal to —$(CHR^{19})_n$—, —W—CO—NH—$(CHR^{19})_n$—, —Y—CO—NH—$R^{18}$—, —$(CHR^{19})_n$—, —$SR^{18}$—, —CO—O—$R^{18}$— or is absent, with n being equal to 1 to 4, $R^{19}$ is hydrogen, $C_1$ to $C_{10}$ alkyl or $C_6$ to $C_{10}$ aryl, V has one of the meanings given for $R^{14}$ and W stands for an O or S atom or is absent; with $R^{18}$ and $R^{19}$ being able to be substituted or unsubstituted; $R^{20}$ is a hydrolyzable group; d, e, f and x each independently of each other being 1, 2 or 3; and the sum of d+x=2 to 4.

In another embodiment the low shrinkage resins include those described in U.S. Pat. No. 8,710,113 (Eckert et al.) comprising a hardenable compound, which contains a comparable rigid backbone unit, a spacer unit and a unit comprising polymerizable endgroups being connected to the spacer unit via urethane moieties and exemplified by the compound:

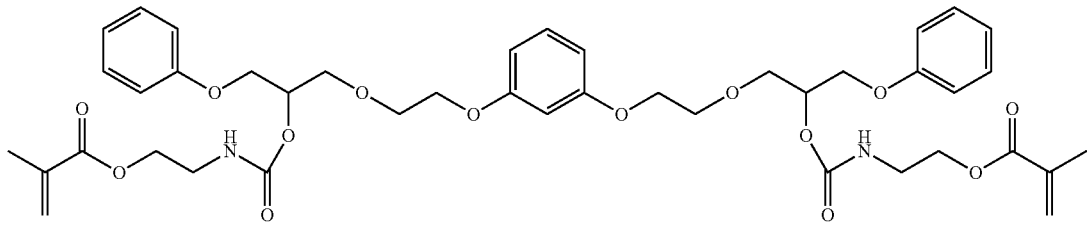 [SMILES: C=C(C)C(=O)OCCNC(=O)OC(COCCOc1cccc(OCCOCC(COc2ccccc2)OC(=O)NCCOC(=O)C(=C)C)c1)COc1ccccc1]

The multifunctional low shrinkage resins are (e.g. highly) viscous liquids at about 25° C., yet are flowable. The viscosity as can be measured with a Haake RotoVisco RV1 device, as described in EP Application No. 10168240.9, filed Jul. 2, 2010 is typically at least 300, or 400, or 500 Pa*s and no greater than 10,000 Pascal-seconds (Pa*s). In some embodiments, the viscosity is no greater than 5000 or 2500 Pa*s.

The ethylenically unsaturated resins of the dental composition are typically stable liquids at about 25° C. meaning that the resins do not substantially polymerize, crystallize, or otherwise solidify when stored at room temperature (about 25° C.) for a typical shelf life of at least 30, 60, or 90 days. The viscosity of the resins typically does not change (e.g. increase) by more than 10% of the initial viscosity.

Particularly for dental restoration compositions, the ethylenically unsaturated resins generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight resin lacking such substituents).

In some embodiments, the (unfilled) polymerizable resin may comprise solely one or more low shrink resins in combination with the photoinitiator. In other embodiments, the (unfilled) polymerizable resin comprises a small concentration of other monomer(s). By "other" is it meant an ethylenically unsaturated monomer such as a (meth)acrylate monomer that is not a low volume shrinkage monomer.

The concentration of such other monomer(s) is typically no greater than 20 wt. %, 19 wt. %, 18 wt. %, 17 wt. %, 16 wt. %, or 15 wt. % of the (unfilled) polymerizable resin portion. The concentration of such other monomers is typically no greater than 5 wt. %, 4 wt. %, 3 wt. %, or 2 wt. % of the filled polymerizable dental composition.

In some embodiments, the "other monomers" of the dental composition comprise a low viscosity reactive (i.e. polymerizable) diluent. Reactive diluents typically have a viscosity of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

In some embodiments, the reactive diluent is an isocyanurate or tricyclodecane monomer. Tricyclodecane reactive diluent may have the same generally structure as previously described. In favored embodiments, the tricyclodecane reactive diluent comprises one or two spacer unit(s) (S) being connected to the backbone unit (U) via an ether linkage; such as described in U.S. 2011/041736 (Eckert et al.); incorporated herein by reference.

The curable component of the curable dental composition can include a wide variety of "other" ethylenically unsaturated compounds (with or without acid functionality), epoxy-functional (meth)acrylate resins, vinyl ethers, and the like.

The polymerizable dental compositions may include free radically polymerizable monomers, agents, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof.

Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri (meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra (meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and tri shydroxyethyl-isocyanurate tri (meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups as an example of an "other monomer". Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are available from a wide variety of commercial sources, such as Sigma-Aldrich, St. Louis.

The curable dental compositions can include at least 1 wt. %, at least 3 wt. %, or at least 5 wt. % ethylenically unsaturated compounds with hydroxyl functionality, based on the total weight of the unfilled composition. The compositions can include at most 80 wt. %, at most 70 wt. %, or at most 60 wt. % ethylenically unsaturated compounds with hydroxyl functionality.

The dental compositions described herein may include one or more curable components in the form of ethylenically unsaturated compounds with acid functionality as an example of an "other" monomer. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. Such acid-functional "other" monomers contribute to the self-adhesion or self-etching of the dental compositions as described in U.S. 2005/017966 (Falsafi et al.), incorporated herein by reference.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth) acrylate (e.g., HEMA) phosphates, bis((meth)acryloxyethyl) phosphate, bis((meth)acryloxypropyl) phosphate, bis((meth) acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly (meth)acrylated polyboric acid, and the like, may be used as components. Also, monomers, oligomers, and polymers of unsaturated carbonic acids such as (meth)acrylic acids, itaconic acid, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth) acryloxy group and at least one —O—P(O)(OH)$_x$ group, wherein x=1 or 2, and wherein the at least one —O—P(O) (OH)$_x$ group and the at least one (meth)acryloxy group are linked together by a $C_1$-$C_4$ hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_5$-$C_{12}$ hydrocarbon group; an ethylenically unsaturated compound without acid functionality; an initiator system; and a filler.

The curable dental compositions can include at least 1 wt. %, at least 3 wt. %, or at least 5 wt. % ethylenically unsaturated compounds with acid functionality, based on the total weight of the unfilled composition. The compositions can include at most 80 wt. %, at most 70 wt. %, or at most 60 wt. % ethylenically unsaturated compounds with acid functionality.

The curable dental compositions may include resin-modified glass ionomer cements such as those described in U.S. Pat. No. 5,130,347 (Mitra), U.S. Pat. No. 5,154,762 (Mitra), U.S. Pat. No. 5,925,715 (Mitra et al.) and U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are contemplated.

Curing is effected by exposing the composition to a radiation source, preferably a UV light source. It is convenient to employ light sources that emit actinic radiation light between 250 nm and 800 nm (particularly blue light of a wavelength of 320-400 nm) such as quartz halogen lamps, tungsten-halogen lamps, mercury arcs, carbon arcs, low-, medium-, and high-pressure mercury lamps, plasma arcs, light emitting diodes, UV LEDs and lasers. In general, useful light sources have intensities in the range of 500-1500 mW/cm$^2$. A variety of conventional lights for hardening such compositions can be used.

The exposure may be accomplished in several ways. Although the polymerizable composition may be continuously exposed to radiation throughout the entire hardening process (e.g., about 2 seconds to about 60 seconds), the instant initiator system allows one to expose the composition to a single dose of radiation, and then remove the radiation source, thereby allowing polymerization to occur.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Suitable inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. Nos. 7,156,911; and 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprises a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 75 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1041, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO™ 1042 or 2327.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The primary particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like and may comprise silane, zirconate or titanate coupling agents. Preferred coupling agents include gamma-methacryloxypropyltrimethoxysilane, gamma-mercaptopropyltriethoxysilane, gamma-aminopropyltrimethoxysilane, and the like.

Suitable copolymerizable or reactive organometallic compounds may have the general formulas: $CH_2=C(R^{22})—R^{21}Si(OR)_nR_{3-n}$ or $CH_2=C(R^{22})—C=\!=\!OOR^{21}Si(OR)_nR_{3-n}$; wherein R is an $C_1$-$C_4$ alkyl, $R^{21}$ is a divalent organic heterohydrocarbyl linking group, preferably alkylene; $R^{22}$ is H or C1-C4 alkyl; and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, the dental compositions can have an initial color different than the cured dental structures. Color can be imparted to the composition through the use of a photobleachable or thermochromic dye. As used herein, "photobleachable" refers to loss of color upon exposure to actinic radiation. The composition can include at least 0.001 wt. % photobleachable or thermochromic dye, and typically at least 0.002 wt. % photobleachable or thermochromic dye, based on the total weight of the composition. The composition typically includes at most 1 wt. % photobleachable or thermochromic dye, and more typically at most 0.1 wt. % photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin Bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be cured into dental articles prior to applying. For example, a dental article such as a crown may be pre-formed from the curable dental composition described herein. Dental composite (e.g. crowns) articles can be made from the curable composition described herein by casting the curable composition in contact with a mold and curing the composition. Alternatively, dental composites or articles (e.g. crowns) can be made by first curing the composition forming a mill blank and then mechanically milling the composition into the desired article.

Another method of treating a tooth surface comprises providing a dental composition as described herein wherein the composition is in the form of a (partially cured) curable, self-supporting, malleable structure having a first semi-finished shape; placing the curable dental composition on a tooth surface in the mouth of a subject; customizing the shape of the curable dental composition; and hardening the curable dental composition. The customization can occur in the patient's mouth or on a model outside the patient mouth such as described in U.S. Pat. No. 7,674,850 (Karim et al.); incorporated herein by reference.

EXAMPLES

TABLE 1

| Materials | | |
|---|---|---|
| Designation | Description | Source |
| | acetone | OmniSolv, EMD, Philadelphia, PA |
| MeCN | acetonitrile | Sigma Aldrich, St. Louis, MO |
| | benzoyl chloride | Sigma Aldrich |
| BisGMA | bisphenol A glycerolate dimethacrylate | Sigma Aldrich |
| | 2,3-butanediol | TCI America, Porland, OR |
| $Cs_2CO_3$ | cesium carbonate | Alfa Aesar, Ward Hill, MA |
| Cu(I)I | copper iodide | Sigma Aldrich |
| $Pd(PPh_3)_2Cl_2$ | dichlorobis(triphenylphosphine)palladium(II) | Strem Chemical, Newburyport, MA |
| DDQ | 2,3-dichloro-5,6-dicyano-1,4-benzoquinone | Alfa Aesar |

TABLE 1-continued

Materials

| Designation | Description | Source |
|---|---|---|
| IRGACURE 651 | 2,2-Dimethoxy-2-phenylacetophenone, available under the trade designation "IRGACURE 651" | Sigma Aldrich |
| IRGACURE 819 | Bis(2,4,6-trimethylbenzoyl)-phenylphosphineoxide, available under the trade designation "IRGACURE 819" | BASF, Florham Park, NJ |
| | 2,5-dimethylbenzyl chloride | Sigma Aldrich |
| | 2,2-dimethyl-1,3-propanediol | Alfa Aesar |
| EtOAc | ethyl acetate | OmniSolv, EMD |
| | ethylene glycol | Sigma Aldrich |
| $MgSO_4$ | magnesium sulfate | EMD |
| | 2-methoxybenzyl chloride | Sigma Aldrich |
| | 4-methoxybenzyl chloride | Sigma Aldrich |
| | phenylacetylene | Alfa Aesar |
| $KMnO_4$ | potassium permanganate | Alfa Aesar |
| $Sc(OTf)_3$ | scandium triflate | Strem Chemicals |
| $NaHCO_3$ | sodium bicarbonate | Macron, Center Valley, PA |
| $NaNO_2$ | sodium nitrite | Sigma Aldrich |
| $Na_2SO_4$ | sodium sulfate | JT Baker, Center Valley, PA |
| $H_2SO_4$ | sulfuric acid | JT Baker |
| | toluene | Alfa Aesar |
| p-TsOH | p-toluene sulfonic acid | JT Baker |
| TEA, $Et_3N$ | triethylamine | Sigma Aldrich |
| TEGDMA | triethylene glycol dimethacrylate | TCI |
| | [4-(Trifluoromethyl)phenyl](trimethylsilyl)acetylene | Sigma Aldrich |
| TMPTA | Trimethylolpropane triacrylate | Alfa Aesar |
| TMPTMA | Trimethylolpropane trimethacrylate | TCI |
| $CH(OCH_3)_3$ | trimethylorthoformate | Sigma Aldrich |
| TPO-L | Ethyl (2,4,6-trimethylbenzoyl) phenylphosphinate | BASF |
| XPHOS | 2-Dicyclohexylphosphino-2',4',6'-triisopropylbiphenyl, available under the trade designation "XPHOS" | Strem Chemicals |

Example 1 (EX-1): Synthesis of 1-(2-(4-methoxyphenyl)-1,3-dioxolan-2-yl)-2-phenylethane-1,2-dione

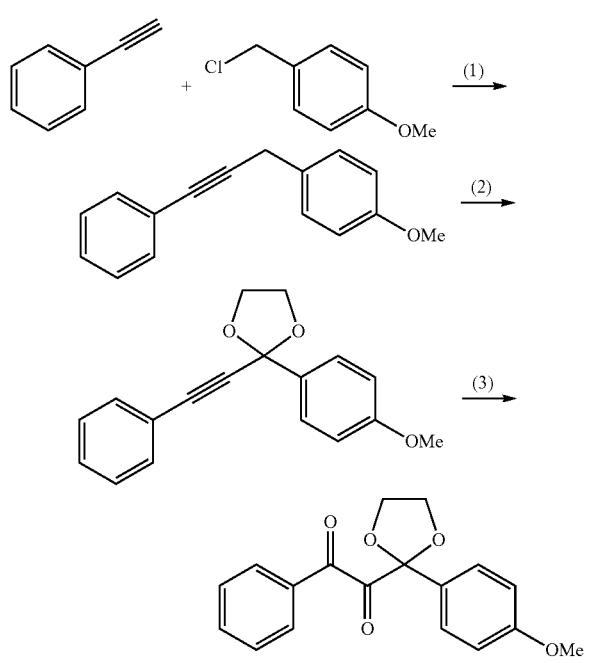

Step 1: A benzylalkyne was synthesized according to literature procedure (Larsen, C. H., et al., Synlett, 2006, vol. 18, pp. 2941-2946). Into a round bottom flask with a stir bar was placed palladium(II)acetate (0.224 g, 1.00 mmol), XPHOS (1.43 g, 3.00 mmol), and cesium carbonate (17.1 g, 53.5 mmol). The flask was fitted with a rubber septum and evacuated and backfilled with $N_2$ three times. Acetonitrile (125 mL) was added followed by 4-methoxybenzyl chloride (6.75 mL, 50 mmol) and phenylacetylene (7 mL, 65 mmol). The reaction mixture stirred at room temperature for 4 h. After such time the mixture was concentrated, diluted with EtOAc, filtered over CELITE and concentrated. Purification via automatic flash column chromatography (BIOTAGE ISOLERA) afforded a dark red liquid (11.0 g, 99% yield).

Step 2: The ketal was synthesized according to literature procedure (Mo, H.; Bao, W., Tetrahedron, 2011, volume 67, pp. 4793-4799). The benzylalkyne (1.80 g, 8.08 mmol) from Step 1 was dissolved in $CH_2C_{12}$ (32 mL) in a round bottom flask equipped with a stir bar. The mixture was cooled to 0° C. and ethylene glycol (0.54 mL, 9.70 mmol) was added, followed by DDQ (3.76 g, 16.6 mmol) portionwise. The reaction was allowed to warm to room temperature and stir for 1 hr. After such time, the mixture was filtered over CELITE, concentrated and purified via flash column purification. A pale yellow solid was obtained (200 mg, 6% yield) containing the product of interest along with an impurity (~50%).

Step 3: The alkyne was oxidized according to literature procedure (Srinivasan, N. S.; Lee, D. G. J. Org. Chem. 1979, volume 44, p. 1574). The mixture from Step 2 (0.067 g) was stirred in acetone (9.5 mL) in a 1 dram vial equipped with a stir bar. A solution of $MgSO_4$ (0.057 g, 0.475 mmol) and $NaHCO_3$ (0.060 g, 0.71 mmol) in water (5.3 mL) was added to the mixture, followed by $KMnO_4$ (0.146 g, 0.93 mmol).

The reaction stirred at room temperature for 2 h and then quenched by adding small volumes of NaNO$_2$ and 10% by volume aqueous H$_2$SO$_4$ slowly until the brown mixture turned homogeneous and yellow. The reaction mixture was extracted with EtOAc (3×), washed with saturated aqueous NaHCO$_3$ and brine, dried (Na$_2$SO$_4$), concentrated and purified by flash column chromatography. A yellow oil was isolated (0.030 g, 50% yield) that was free from any impurities.

Example 2 (EX-2): Synthesis of 1-(2-(2-methoxyphenyl)-1,3-dioxolan-2-yl)-2-phenylethane-1,2-dione

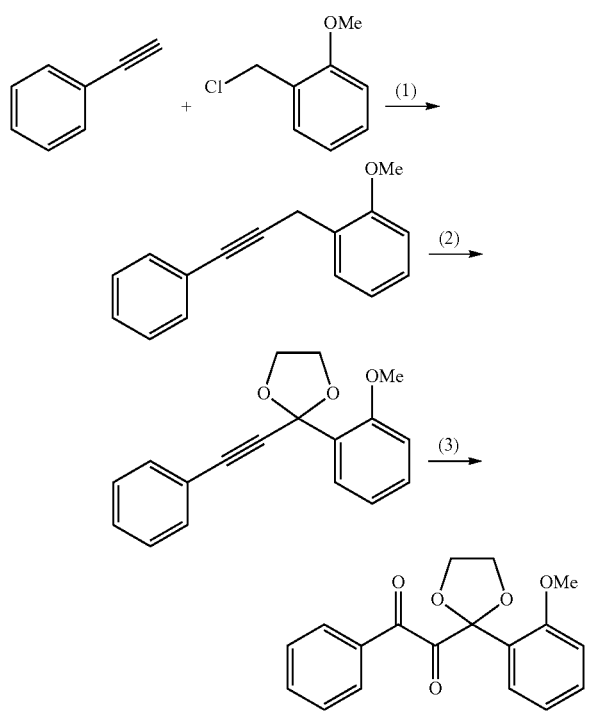

Step 1 and Step 2: 2-(4-methoxyphenyl)-2-(phenylethynyl)-1,3-dioxolane was synthesized according to literature procedures (Larsen, C. H., et al., Synlett, 2006, volume 18, pp. 2941-2946; and Mo, H.; Bao, W., Tetrahedron, 2011, volume 67, pp. 4793-4799), following the steps described for EX-1, except starting with 2-methoxybenzyl chloride.
Step 3: The alkyne was oxidized according to literature procedure (Srinivasan, N. S.; Lee, D. G. J. Org. Chem. 1979, volume 44, p. 1574). 2-(4-Methoxyphenyl)-2-(phenylethynyl)-1,3-dioxolane (0.063 g, 0.220 mmol) was stirred in acetone (9.0 mL) in a 1 dram vial equipped with a stir bar. A solution of MgSO$_4$ (0.053 g, 0.44 mmol) and NaHCO$_3$ (0.055 g, 0.66 mmol) in water (5.3 mL) was added to the mixture, followed by KMnO$_4$ (0.136 g, 0.86 mmol). The reaction stirred at room temperature for 2 h and then quenched by adding small volumes of NaNO$_2$ and 10% by volume aqueous H$_2$SO$_4$ slowly until the brown mixture turned homogeneous and yellow. The reaction mixture was extracted with EtOAc (3×), washed with saturated aqueous NaHCO$_3$ and brine, dried (Na$_2$SO$_4$), concentrated and purified by flash column chromatography. A yellow oil was isolated (0.060 g, 87% yield).

Example 3 (EX-3): Synthesis of 1-(2-(2,5-dimethylphenyl)-1,3-dioxolan-2-yl)-2-phenylethane-1,2-dione

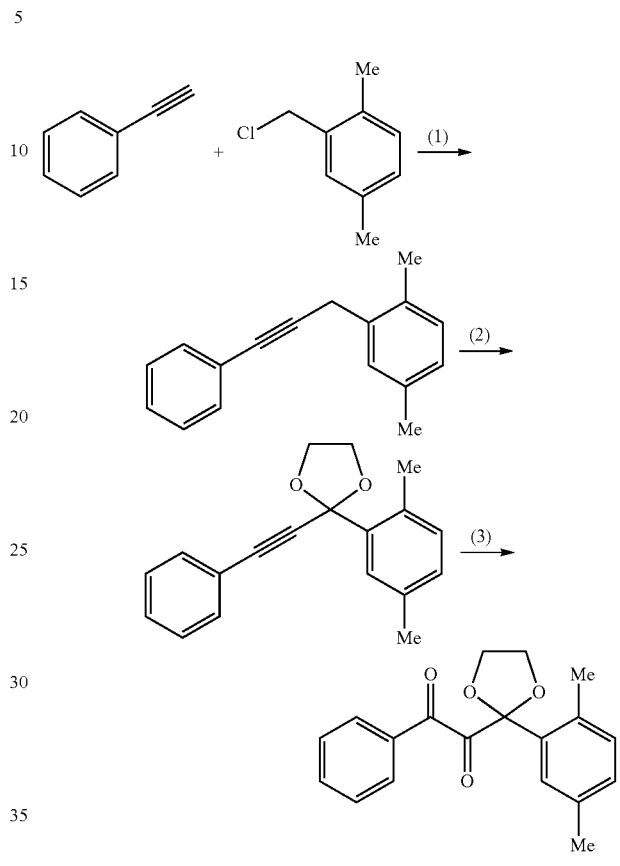

Step 1: 1,4-dimethyl-2-(3-phenylprop-2-yn-1-yl)benzene was prepared in a similar fashion as formation of the benzylalkyne in Step 1 of EX-1 (1.10 g, 99% yield), except starting with 2,5-dimethylbenzyl chloride.
Step 2: 2-(2,5-dimethylphenyl)-2-(phenylethynyl)-1,3-dioxolane was prepared in similar fashion as the ketal formation in Step 2 of EX-1. The benzylalkyne (1.10 g, 5.0 mmol) from Step 1 was dissolved in CH$_2$C$_{12}$ (20 mL) in a round bottom flask equipped with a stir bar. The mixture was cooled to 0° C. and ethylene glycol (0.33 mL, 5.92 mmol) was added, followed by DDQ (2.32 g, 10.2 mmol) portionwise. The reaction was allowed to warm to room temperature and stir for 1 hr. After such time, the mixture was filtered over CELITE, concentrated and purified via automatic flash column purification. A pale yellow oil was obtained (0.250 g, 18% yield).
Step 3: The alkyne was oxidized according to literature procedure (Srinivasan, N. S.; Lee, D. G. J. Org. Chem. 1979, volume 44, p. 1574). The product from Step 2 (0.250 g, 0.90 mmol) was stirred in acetone (36 mL) in a 1 dram vial equipped with a stir bar. A solution of MgSO$_4$ (0.216 g, 1.80 mmol) and NaHCO$_3$ (0.226 g, 2.69 mmol) in water (20 mL) was added to the mixture, followed by KMnO$_4$ (0.553 g, 3.50 mmol). The reaction stirred at room temperature for 2 h and then quenched by adding small volumes of NaNO$_2$ and 10% by volume aqueous H$_2$SO$_4$ slowly until the brown mixture turned homogeneous and yellow. The reaction mixture was extracted with EtOAc (3×), washed with saturated aqueous NaHCO$_3$ and brine, dried (Na$_2$SO$_4$), concentrated and purified by flash column chromatography. A yellow oil was isolated (0.150 g, 54% yield).

Example 4 (EX-4): Synthesis of 1-(2-(4-methoxy-phenyl)-5,5-dimethyl-1,3-dioxan-2-yl)-2-phenyle-thane-1,2-dione Example 5 (EX-5): Synthesis of 1-(2-(2-methoxy-phenyl)-5,5-dimethyl-1,3-dioxan-2-yl)-2-phenyle-thane-1,2-dione

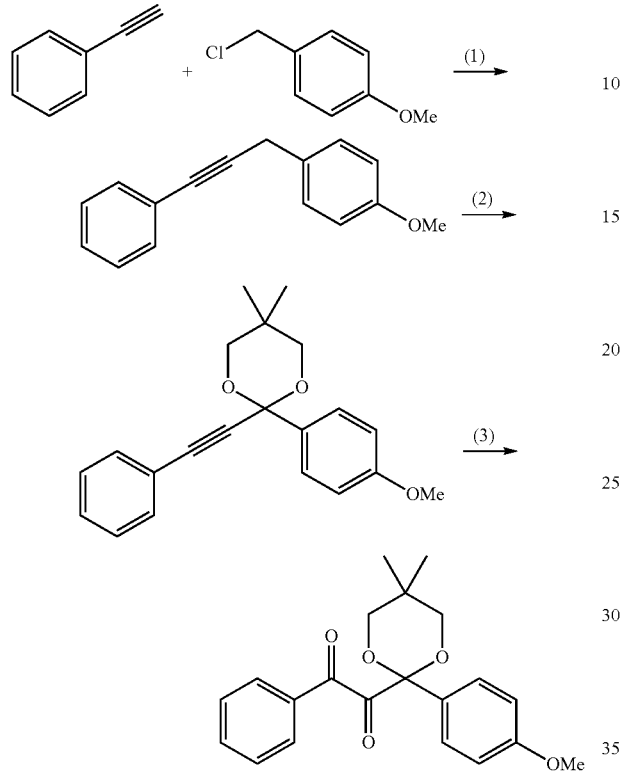

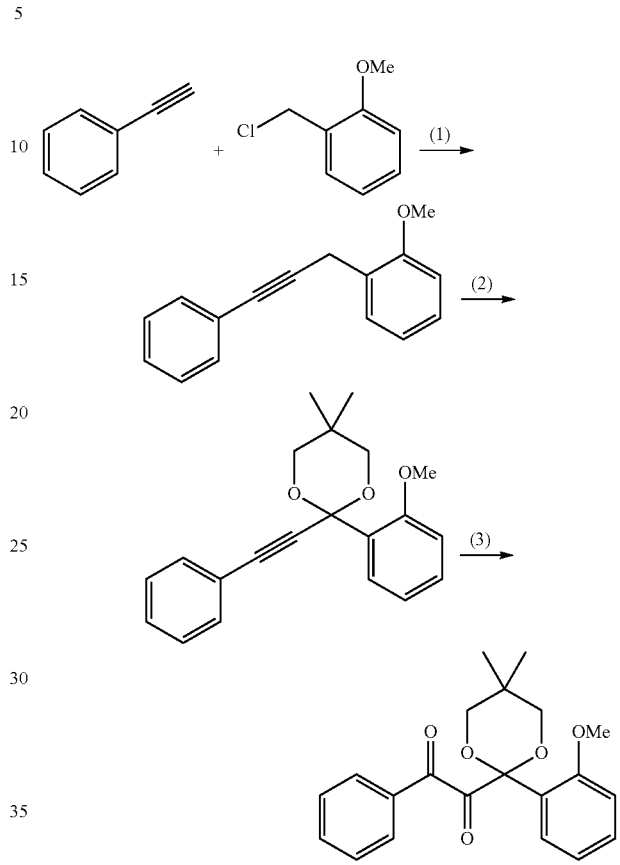

Step 1: 4-methoxy-(3-phenylprop-2-yn-1-yl)benzene was prepared as in Step 1 of EX-1.

Step 2: 2-(4-methoxyphenyl)-5,5-dimethyl-2-(phenyl-ethynyl)-1,3-dioxane was prepared in similar fashion as in Step 2 of Example 1. The benzylalkyne (0.250 g, 1.0 mmol) from Step 1 was dissolved in CH$_2$C$_{12}$ (4 mL) in a vial equipped with a stir bar. The mixture was cooled to 0° C. and 2,2-dimethyl-1,3-propanediol (0.125 g, 1.2 mmol) was added, followed by DDQ (0.465 g, 2.05 mmol) portionwise. The reaction was allowed to warm to room temperature and stir for 2 hr. After such time, the mixture was filtered over CELITE, concentrated and purified via automatic flash column purification. A yellow oil was obtained (0.117 g, 36% yield).

Step 3: The alkyne was oxidized according to literature procedure (Srinivasan, N. S.; Lee, D. G. J. Org. Chem. 1979, volume 44, p. 1574). The product from Step 2 (0.110 g, 0.34 mmol) was stirred in acetone (13 mL) in a 1 dram vial equipped with a stir bar. A solution of MgSO$_4$ (0.082 g, 68 mmol) and NaHCO$_3$ (0.086 g, 1.02 mmol) in water (8 mL) was added to the mixture, followed by KMnO$_4$ (0.210 g, 1.3 mmol). The reaction stirred at room temperature for 2 h and then quenched by adding small volumes of NaNO$_2$ and 10% by volume aqueous H$_2$SO$_4$ slowly until the brown mixture turned homogeneous and yellow. The reaction mixture was extracted with EtOAc (3×), washed with saturated aqueous NaHCO$_3$ and brine, dried (Na$_2$SO$_4$), concentrated and purified by flash column chromatography. A yellow solid was isolated (0.100 g, 83% yield).

Step 1: 4-methoxy-(3-phenylprop-2-yn-1-yl)benzene was prepared as in Step 1 of EX-2.

Step 2: 2-(2-methoxyphenyl)-5,5-dimethyl-2-(phenyl-ethynyl)-1,3-dioxane was prepared in similar fashion as Step 2 of EX-4. The benzylalkyne (0.667 g, 3.0 mmol) from Step 1 was dissolved in CH$_2$C$_{12}$ (12 mL) in a vial equipped with a stir bar. The mixture was cooled to 0° C. and 2,2-dimethyl-1,3-propanediol (0.375 g, 3.6 mmol) was added, followed by DDQ (1.40 g, 6.2 mmol) portionwise. The reaction was allowed to warm to room temperature and stir for 2 hr. After such time, the mixture was filtered over CELITE, concentrated and purified via automatic flash column purification. A brown solid was obtained (0.153 g, 16% yield).

Step 3: The alkyne was oxidized according to literature procedure (Srinivasan, N. S.; Lee, D. G. J. Org. Chem. 1979, volume 44, p. 1574). The product from Step 2 (0.153 g, 0.47 mmol) was stirred in acetone (19 mL) in a 1 dram vial equipped with a stir bar. A solution of MgSO$_4$ (0.114 g, 0.95 mmol) and NaHCO$_3$ (0.120 g, 1.42 mmol) in water (10 mL) was added to the mixture, followed by KMnO$_4$ (0.293 g, 1.8 mmol). The reaction stirred at room temperature for 2 h and then quenched by adding small volumes of NaNO$_2$ and 10% by volume aqueous H$_2$SO$_4$ slowly until the brown mixture turned homogeneous and yellow. The reaction mixture was extracted with EtOAc (3×), washed with saturated aqueous NaHCO$_3$ and brine, dried (Na$_2$SO$_4$), concentrated and purified by flash column chromatography. A yellow solid was isolated (0.137 g, 81% yield).

Example 6 (EX-6): Synthesis of 1-(2-(4-methoxyphenyl)-4,5-dimethyl-1,3-dioxolan-2-yl)-2-phenylethane-1,2-dione

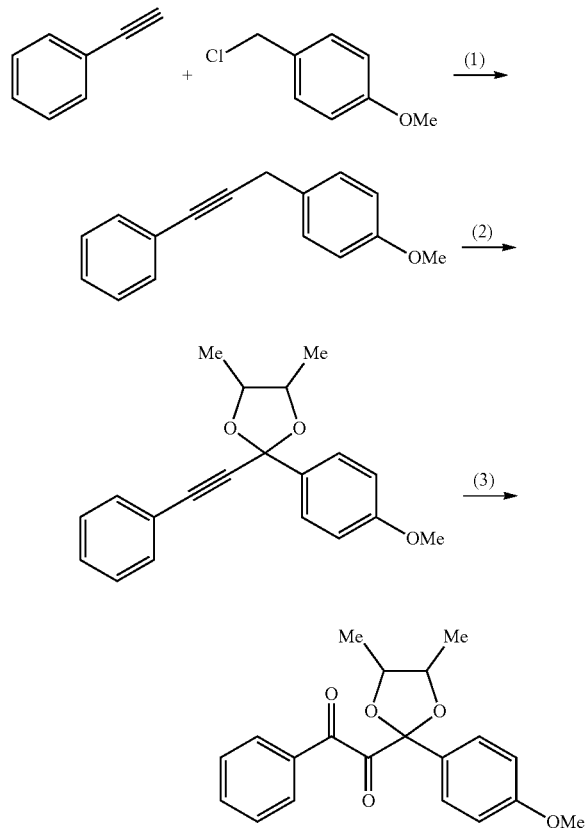

Step 1: 4-methoxy-(3-phenylprop-2-yn-1-yl)benzene was prepared as in Step 1 of EX-1.

Step 2: The benzylalkyne (0.445 g, 2.0 mmol) from Step 1 was dissolved in $CH_2Cl_2$ (8 mL) in a vial equipped with a stir bar. The mixture was cooled to 0° C. and 2,3-butanediol (0.22 mL, 2.4 mmol) was added, followed by DDQ (0.931 g, 4.1 mmol) portionwise. The reaction was allowed to warm to room temperature and stir for 2 hr. After such time, the mixture was filtered over CELITE, concentrated and purified via automatic flash column purification. A yellow oil was obtained (0.082 g, 18% yield).

Step 3: The alkyne was oxidized in a method similar to that used in Step 3 of EX-5. The product from Step 2 (0.059 g, 0.19 mmol) was stirred in acetone (7.6 mL) in a vial equipped with a stir bar. A solution of $MgSO_4$ (0.046 g, 0.38 mmol) and $NaHCO_3$ (0.048 g, 0.51 mmol) in water (4.2 mL) was added to the mixture, followed by $KMnO_4$ (0.117 g, 0.74 mmol). The reaction stirred at room temperature for 2 h and then quenched by adding small volumes of $NaNO_2$ and 10% by volume aqueous $H_2SO_4$ slowly until the brown mixture turned homogeneous and yellow. The reaction mixture was extracted with EtOAc (3×), washed with saturated aqueous $NaHCO_3$ and brine, dried ($Na_2SO_4$), concentrated and purified by flash column chromatography. A yellow solid was isolated (0.024 g, 37% yield).

Example 7 (EX-7): Synthesis of 1-(2-phenyl-1,3-dioxolan-2-yl)-2-(4-(trifluoromethyl)phenyl)-ethane-1,2-dione

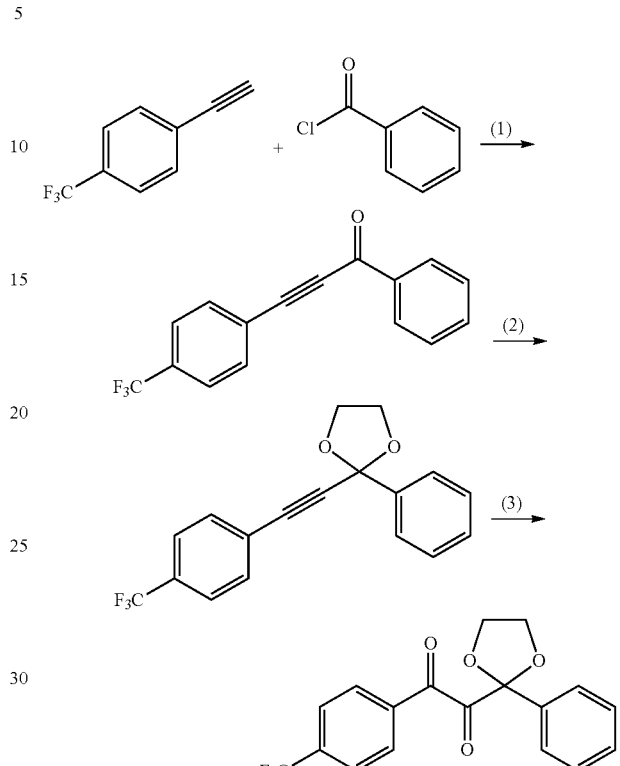

Step 1: A literature preparation was followed (Chem. Commun., 2005, pp. 1037-1039). To a solution of benzoyl chloride (0.92 mL, 7.9 mmol) and 1-ethynyl-4-(trifluoromethyl)benzene (prepared from [4-(trifluoromethyl)phenyl] (trimethylsilyl)acetylene) (0.90 g, 5.3 mmol) in anhydrous tetrahydrofuran (10 mL), under a $N_2$ atmosphere, was added dichlorobis(triphenylphosphine)palladium(II) (38 mg, 0.054 mmol) then copper(I)iodide (30 mg, 0.005 mmol). After 1 min of stirring triethylamine (0.96 mL, 6.9 mmol) was added and the reaction left to stir for 40 min at rt. The reaction was then diluted with EtOAc and washed with water. The aqueous layer was then extracted with EtOAc and all organics combined and dried ($Na_2SO_4$). The suspension was then filtered, concentrated and purified by flash chromatography. A pale yellow solid was obtained (0.91 g, 63% yield).

Step 2: The cyclic ketal was formed in a two-step process. The alkynone from Step 1 (100 mg, 0.365 mmol) was dissolved in anhydrous MeOH (0.55 mL). To this was added trimethylorthoformate (0.28 mL, 2.55 mmol) and p-toluene sulfonic acid (7 mg, 0.037 mmol) and the reaction stirred at room temperature overnight. After such time, the volatiles were removed in vacuo. Molecular sieves (3 Å), toluene (0.5 mL) and scandium triflate (16 mg, 0.036 mmol) were added and the reaction heated to 80° C. for 3 hours. The reaction mixture was cooled to room temperature and loaded onto a silica cartridge and purified by automated flash column chromatography. A colorless oil was obtained (39.3 mg, 34% yield) along with the starting alkynone (37.1 mg, 37% recovered).

Step 3: The alkyne was oxidized in a method similar to that used in Step 3 of EX-5. The product from Step 2 (0.034 g, 0.11 mmol) was stirred in acetone (4.2 mL) in a vial equipped with a stir bar. A solution of $MgSO_4$ (0.026 g, 0.21 mmol) and NaHCO$_3$ (0.027 g, 0.32 mmol) in water (2.3 mL) was added to the mixture, followed by KMnO$_4$ (0.065 g, 0.41 mmol). The reaction stirred at room temperature for 2 h and then quenched by adding small volumes of NaNO$_2$ and 10% by volume aqueous H$_2$SO$_4$ slowly until the brown mixture turned homogeneous and yellow. The reaction mixture was extracted with EtOAc (3×), washed with saturated aqueous NaHCO$_3$ and brine, dried (Na$_2$SO$_4$), concentrated and purified by flash column chromatography. A yellow solid was isolated (0.07 g, 18% yield).

Curing Studies: Curing with acrylate TMPTA resin at 365, 385, and 400 nm LEDs

The ketal diketone compounds of Examples 1 to 6 were tested for photoinitiating ability using TMPTA (a trifunctional acrylate resin) with 1 wt. % of ketal diketone. The compound was added to the resin and placed in a sonicator or vortexed until complete dissolution was observed. The resin mixture was placed between two glass slides using a 10 mil (about 254 micrometers) spacer and subjected to near-infrared spectroscopy studies using a spot LED of 365, 385 or 400 nm. The area under the peak corresponding to the acrylate (6100-6240 cm$^{-1}$) was integrated before and after exposure to an LED light. They were compared to the commercially available UV photoinitiator, TPO-L, which is a phosphine oxide based photoinitiator. Results of the curing test were as summarized in Table 2.

TABLE 2

Curing results, 1 wt. % in TMPTA, 40 second exposure

| Example | 365 nm, percent cure | 385 nm, percent cure | 400 nm, percent cure |
|---|---|---|---|
| EX-1 | 31 | 33 | 10 |
| EX-2 | 36 | 44 | 20 |
| EX-3 | 21 | 34 | 21 |
| EX-4 | 33 | 36 | 28 |
| EX-5 | 31 | 39 | 4 |
| EX-6 | 28 | 30 | 8 |
| CE-1 | 79 | 63 | 64 |

All compounds showed the highest reactivity with the 385 nm LED, compared to the standard, TPO-L, in which reactivity slightly decreased with the longer wavelength. The 6-membered dioxane ring (EX-4) showed comparable reactivity despite the expansion of the ketal ring from a 5-membered ring to a 6-membered ring Curing with acrylate TMPTA resin as a real-time series A real-time series was obtained in which samples were continuously irradiated with a 385 nm LED light source, and conversion of the acrylate functionality was monitored by infrared ("IR") spectroscopy (integrating IR absorption the area from 6230-6103 cm$^{-1}$) as a function of time. The ketal diketone initiators of EX-4 and EX-6 were evaluated along with a standard photoinitiator, IRGACURE 651 ("CE-2"). All sample materials were present as 1 wt. % in TMPTA resin. The results were as summarized in FIG. 1. For the experimental data shown in FIG. 1, the 385 nm LED light source was turned on after 10 seconds of monitoring.

Example 4C: Curing with Methacrylate TMPTMA Resin as a Real-Time Series

Figure 2:
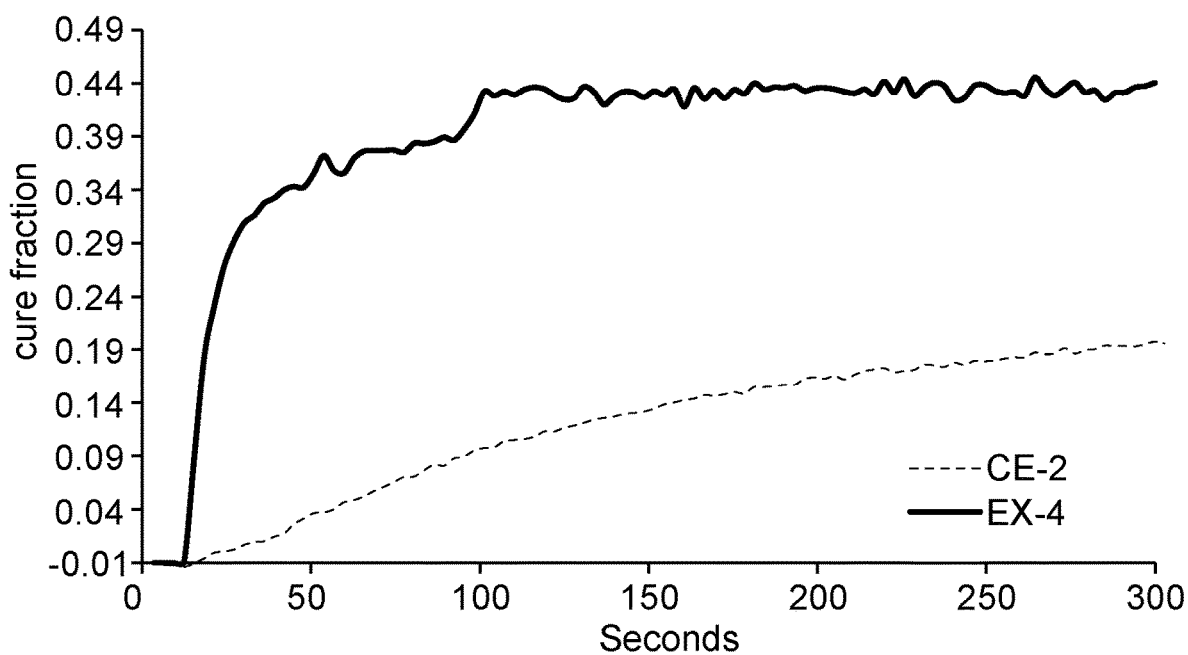
FIG. 2 is the IR spectra of a polymerization using the protected photoinitiator of Example 4 compared to Comparative Example 2.

A real-time series was performed with the ketal diketone initiator of EX-4 in a trifunctional methacrylate resin (TMPTMA) with a 385 nm LED. Approximately 20% cure was observed after 5 min. of exposure, compared to CE-2 which reached its maximum cure of 45% under 2 min., as shown in FIG. 2.

Curing Studies: Curing with acrylate TMPTA resin at 365, 385, and 400 nm LEDs

The ketal diketone compound of Example 1 was tested for photoinitiating ability using 1:1 TEGDMA/BisGMA resin with 1 wt. % of the ketal diketone of EX-1. The compound was added to the resin and placed in a sonicator or vortexed until complete dissolution was observed. The resin mixture was placed between two glass slides using a 10 mil (about 254 micrometers) spacer and subjected to near-infrared spectroscopy studies using a spot LED of 385 nm. The area under the peak corresponding to the acrylate (6230-6103 cm$^{-1}$) was integrated before and after exposure to an LED light. They were compared to the commercially available UV photoinitiators IRGACURE 651 ("CE-2") and IRGACURE 819 ("CE-3"). Results of the curing test were as summarized in Table 3.

TABLE 3

| Photoinitiator | 385 nm, percent cure |
|---|---|
| EX-1 | 15 |
| CE-2 | 64 |
| CE-3 | 68 |

What is claimed is:

1. A protected photoinitiator of the formula:

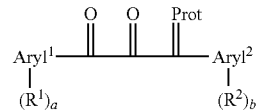

wherein,
Aryl$^1$ is an aromatic or heteroaromatic ring;
Aryl$^2$ is an aromatic ring;
each R$^1$ is an alkyl, an aryl, an electron donating group or an electron withdrawing group, and subscript a is 0 to 3;
each R$^2$ is an alkyl, an aryl, an electron donating group or an electron withdrawing group, and subscript b is 0 to 3;
Prot is a protected carbonyl group.

2. The protected photoinitiator of claim 1 wherein Aryl$^1$ is selected from:

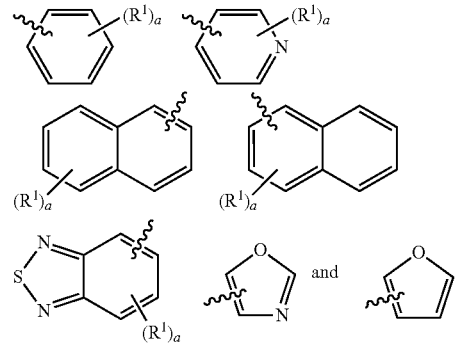

wherein ~ indicated the ring attachment, R$^1$ is an alkyl, an aryl, an electron donating group or an electron withdrawing group, and subscript a is 0 to 3.

3. The protected photoinitiator of claim 1 wherein Aryl$^2$ is selected from phenyl and napthyl.

4. The protected photoinitiator of claim 1 wherein Prot is a cyclic or acyclic ketal.

5. The protected photoinitiator of claim 1 wherein Prot is selected from thioketals, dithioketals, O-substituted cyanohydrins, substituted hydrazones, oxazolidines, imidazolidines or thiazolidines protecting groups.

6. The protected photoinitiator of claim 1 having at least one electron-donating $R^1$ or $R^2$ groups.

7. The protected photoinitiator of claim 1 having at least one electron-withdrawing $R^1$ or $R^2$ groups.

8. A polymerizable composition comprising at least one free-radically polymerizable monomer, and the protected photoinitiator of claim 1.

9. The polymerizable composition of claim 8 wherein the monomer is a (meth)acrylate monomer.

10. The polymerizable composition of claim 8 wherein the monomer is a multifunctional (meth)acrylate monomer.

11. The polymerizable composition of claim 8 comprising
i. up to 100 parts by weight of an (meth)acrylic acid ester;
ii. 0 to 15 parts by weight of an acid functional ethylenically unsaturated monomer;
iii. 0 to 15 parts by weight of a non-acid functional, ethylenically unsaturated polar monomer;
iv. 0 to 5 parts by weight vinyl monomer;
v. 0 to 100 parts by weight of a multifunctional (meth) acrylate relative to i-iv, wherein the sum of I. to Vii is 100%.

12. The polymerizable composition of claim 8 comprising a reactive oligomer having pendent polymerizable groups comprising:
a) greater than 50 parts by weight of (meth)acrylate ester monomer units;
b) 1 to 10 parts by weight of monomer units having a pendent, free-radically polymerizable functional group,
c) 0 to 20 parts by weight of other polar monomer units, wherein the sum of the monomer units is 100 parts by weight.

13. The polymerizable composition of claim 12 wherein the reactive oligomer may be represented by the formula:

where
$[M^{Undatd}]$ represents monomer units having a pendent, free-radically polymerizable functional groups and subscript "o" is the parts be weight thereof;

$[M^{ester}]$ represents (meth)acrylate ester monomer units and subscript "p" represents the parts by weight thereof; and $[M^{polar}]$ represents polar monomer units and subscript "q" represents the parts by weight thereof.

14. The polymerizable composition of claim 8 comprising:
a) 20-80 parts by weight of multifunctional (meth)acrylate monomers and/or multifunctional (meth)acrylate reactive oligomers,
b) 0 to parts by weight range of (meth)acrylate diluent,
c) 20 to 75 wt. % of silica; and
from about 0.1 weight percent to about 5.0 weight percent of the photoinitiator, based on the 100 parts by weight of the polymerizable components of the polymerizable composition.

15. The polymerizable composition of claim 8 further comprising a filler.

16. The polymerizable composition of claim 8 further comprising a chain transfer agent.

17. A curable dental composition comprising a dental resin and the protected photoinitiator of claim 1.

18. A method of making the protected photoinitiator of claim 1 comprising the steps of coupling of an aromatic acetylide compound with an aromatic methylene halide compound, followed by oxidative ketalization, and oxidation of the alkyne to a diketone.

19. A method of making the protected photoinitiator of claim 1 comprising the steps of coupling of an aryl alkyne with an aryl acyl halide, followed by ketalization, then oxidation of the alkyne to a diketone.

20. The protected photoinitiator of claim 1 comprising at least one electron-withdrawing $R^1$ group and at least one electron donating $R^2$ group.

21. The protected photoinitiator of claim 20 wherein the electron donating group is selected from primary amino, secondary amino, tertiary amino, morpholino, hydroxy, alkoxy, aryloxy, alkyl, or combinations thereof, and the electron withdrawing group is selected from halo, cyano, fluoroalkyl, perfluoroalkyl, carboxy, aminocarbonyl, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or combinations thereof.

* * * * *